United States Patent [19]

Alexander et al.

[11] Patent Number: 5,235,007
[45] Date of Patent: Aug. 10, 1993

[54] EPOXY CURING AGENTS

[75] Inventors: David C. Alexander, Austin; Wheeler C. Crawford, Houston; Howard P. Klein, Katy, all of Tex.

[73] Assignee: Texaco Chemical Company, White Plains, N.Y.

[21] Appl. No.: 770,218

[22] Filed: Oct. 3, 1991

[51] Int. Cl.$^5$ .................... C08G 59/14; C08L 63/00
[52] U.S. Cl. .................................... 525/523; 528/93; 528/94
[58] Field of Search .............. 525/523, 528; 528/93, 528/94

[56] References Cited

U.S. PATENT DOCUMENTS

| | | | |
|---|---|---|---|
| 3,236,895 | 2/1966 | Lee et al. | 260/584 |
| 4,122,069 | 10/1978 | Meyer | 528/111 |
| 4,484,994 | 11/1984 | Jacobs, III et al. | 525/504 |
| 4,528,345 | 7/1985 | Waddill | 525/523 |
| 4,543,376 | 9/1956 | Schupp et al. | 525/523 |
| 4,720,569 | 1/1988 | Tominaga | 560/148 |
| 4,775,736 | 10/1988 | Wiggins | 525/523 |
| 4,782,124 | 11/1988 | Hefner, Jr. et al. | 525/523 |
| 4,897,435 | 1/1990 | Jacobs, III et al. | 525/523 |
| 4,935,413 | 6/1990 | Urano et al. | 544/216 |
| 4,977,203 | 12/1990 | Kitabatake | 525/504 |

FOREIGN PATENT DOCUMENTS 1247288 12/1988 Canada .

OTHER PUBLICATIONS

Lee & Neville "Epoxy Resins" pp. 41–44 McGraw Hill Book Co., Inc., 1957.
G. Rokicki, R. Lazinski, Die Angewandte Makromolekulare, Chemie 190 (1989) pp. 211-225.
Kirk-Othmer, Encyclopedia of Chemical Technology, 3rd. Ed., vol. 8, Diuretics to Emulsions–John Wiley & Sons.

*Primary Examiner*—Melvyn I. Marquis
*Assistant Examiner*—Randy Gulakowski
*Attorney, Agent, or Firm*—Jack H. Park; Kenneth R. Priem; Richard A. Morgan

[57] ABSTRACT

An epoxy resin composition comprises the cured reaction product of an epoxy base resin and a curing agent mixture. The curing agent mixture comprises a di-primary amine and a carbamate which is the reaction product of the amine and a cyclic carbonate. The amine has a molecular weight of 60 to 400. Ethylene carbonate and propylene carbonate are the preferred carbonates. The preferred curative comprises a 1:1 to 2:1 molar amine:carbamate mixture.

13 Claims, No Drawings

EPOXY CURING AGENTS

BACKGROUND OF THE INVENTION

1. Field of the Invention

The invention is the cured reaction product of an epoxy resin and a curing agent. The curing agent is a mixture of an aminocarbamate and a di-primary amine.

2. Related Publications in the Art

Epoxy resins constitute a broad class of polymeric materials having a wide range of physical properties. The resins are characterized by epoxide groups, which are cured by reaction with catalysts or curing agents which provide cured epoxy resin compositions with certain desirable properties.

U.S. Pat. No. 3,236,895 to J. M. Lee et al. teaches a series of polyoxyalkylenepolyamines. These di-primary amines are useful for curing epoxy resins.

G. Rokicki, R. Lazinski, *Die Angewandte Makromolekulare Chemie* 190 (1989) pp. 211-225 teaches the reaction products of triethylene tetramine and cyclic carbonates for curing epoxy resins. A 1/1 molar triethylenetetramine-propylene carbonate adduct is reported.

SUMMARY OF THE INVENTION

The invention is an epoxy resin composition comprising the cured reaction product of an epoxy resin and a curing agent. The curing agent is a mixture of a di-primary amine and an aminocarbamate. The aminocarbamate is the reaction product of the di-primary amine and a cyclic carbonate.

The curing agent mixture cured epoxy resins faster than did the di-primary amines alone. The cured epoxy resin compositions displayed mechanical properties which were an improvement over epoxy resins cured with the di-primary amine alone.

DESCRIPTION OF THE PREFERRED EMBODIMENTS

According to the invention an epoxy resin is admixed with a curing amount of a curing agent comprising a mixture of a di-primary amine and an aminocarbamate.

The di-primary amine; which may contain other amine groups, is selected from the group of di-primary amines which are well-known for curing an epoxy base resin. These include ethylene amines, oxyalkylene amines, cycloaliphatic amines and alkylene diamines. Preferably these amines have a molecular weight of 60 to 400.

Ethylene amines include compounds of the structural formula:

$$H_2NCH_2CH_2(NHCH_2CH_2)_xNH_2$$

wherein x ranges from 0 to 5. Examples include monoethylene diamine, diethylene triamine, triethylene tetramine and tetraethylene pentamine all available commercially.

Oxyalkylene amines include ethylene glycol diamines of the structural formula:

wherein x ranges from 0 to 5.

Oxyalkylene amines include propylene glycol diamines of the structural formula:

wherein x ranges from 0 to 6.

Oxyalkylene amines include mixed ethylene glycol-propylene glycol diamines of the structural formula:

wherein A ranges from 1 to 10 and B ranges from 0 to 1.

Cycloaliphatic amines include isophorone diamine of the structural formula:

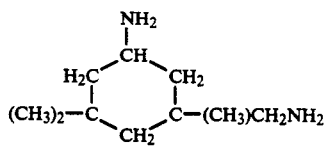

Other examples include 1,3-xylylene diamine and 1,4-xylylene diamine.

Alkylene diamines include 1,3-diamino pentane and 2-methyl-1,5-pentene diamine.

The aminocarbamates of the curing agent mixture are formed by reaction of any of the di-primary amines in the mixture with a cyclic carbonate. Cyclic carbonates of the structural formula:

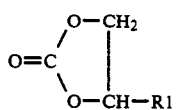

wherein $R_1$ is a radical selected from the group consisting of hydrogen, methyl and ethyl are preferred. Ethylene carbonate and propylene carbonate are most preferred.

The reaction of an ethylene amine with a carbonate yields a mixture of aminocarbamates of the general formulae:

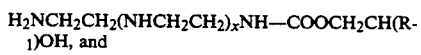

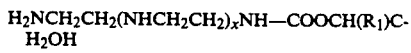

wherein x and $R_1$ are defined by the precursor amine and carbonate.

It is also apparent that when different precursor amines are used, the substructure $(NHCH_2CH_2)_x$ is defined by the amine which is used.

The reaction is carried out by the dropwise addition of the carbonate to the di-primary amine. An excess of amine groups; for example two to three times the stoichiometric requirement, is provided so that unreacted amine remains to form the curative mixture after all of the carbonate is converted to carbamate. The reaction is exothermic, and the addition is carried out at a rate to maintain the reaction mixture temperature at about 70° C. (158° F.). After all of the carbonate is added and the exotherm passes, the reaction mixture is heated for 2 hours at 70° C. (158° F.) to ensure completion. The reaction mixture is then allowed to cool to room temperature and is ready for use as is without separation or other purification for curing an epoxy base resin.

In this regard it is preferred that the reaction be carried out with sufficient excess amine groups so that the cooled reaction mixture has the concentration of amine for producing epoxy resins with optimum properties. If quality control analysis show that the mixture is deficient in amine, more amine is admixed with the cooled reaction mixture to bring it within the inventive amount. It has been found experimentally that the optimal physical properties are achieved when the curing agent reactant mixture comprises a molar ratio of di-primary amine:carbonate of 1.1:1 to 11:1, preferably 2:1 to 3:1. This reactant mixture yields a curing agent mixture comprising a molar ratio of di-primary amine:carbamate of 0.1:1 to 10:1, preferably 1:1 to 2:1.

The preferred epoxy base resin is a vicinal polyepoxide containing compound. Generally the vicinal polyepoxide containing compounds which are amine cured are organic materials having an average of at least 1.8 reactive 1,2-epoxy groups per molecule. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, aromatic halogen atoms and the like. These vicinal polyepoxide containing compounds typically are of an epoxy equivalent weight of 150 to 250. Preferably the base resin, which has an epoxide equivalent weight of from 175 to 195, is derived from condensing epichlorohydrin with 2,2-bis(p-hydroxyphenyl propane) to form 2,2-bis[(p-2,3 epoxy propoxy)phenyl] propane, a derivative of bisphenol A.

Preferred polyepoxides are those of glycidyl ethers prepared by epoxidizing the corresponding allyl ethers or reacting, by known procedures, a molar excess of epichlorohydrin and an aromatic polyhydroxy compound, i.e., isopropylidene bisphenol, novolac, resorcinol, derivatives or aromatic amines, etc. The epoxy derivatives of methylene or isopropylidene bisphenols are especially preferred.

A widely used class of polyepoxides which are useful according to the present invention includes the resinous epoxy polyethers obtained by reacting an epihalohydrin, such as epichlorohydrin, and the like, with either a polyhydric phenol or a polyhydric alcohol. Typically the epoxy resins have an average of at least 1.8 reactive, 1,2-epoxy groups per molecule. An illustrative, but by no means exhaustive, listing of suitable dihydric phenols includes 4,4'-isopropylidene bisphenol, 2,4'-dihydroxydiphenylethylmethane,
3,3'-dihydroxydiphenyldiethylmethane,
3,4'-dihydroxydiphenylmethylpropylmethane,
2,3'-dihydroxydiphenylethylphenylmethane,
4,4'-dihydroxydiphenylpropylphenylmethane,
4,4'-dihydroxydiphenylbutylphenylmethane,
2,2'-dihydroxydiphenylditolylmethane,
4,4'-dihydroxydiphenyltolylmethylmethane
and the like. Other polyhydric phenols which may also be co-reacted with an epihalohydrin to provide these epoxy polyethers are such compounds as resorcinol, hydroquinone, substituted hydroquinones, e.g., methylhydroquinone, and the like.

Among the polyhydric alcohols which can be co-reacted with an epihalohydrin to provide these resinous epoxy polyethers are such compounds as ethylene glycol, propylene glycols, butylene glycols, pentane diols, bis-(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, such as 2,2'-, 3,3'-tetrahydroxydipropylsulfide and the like, mercapto alcohols such as monothioglycerol, dithioglycerol and the like, polyhydric alcohol partial esters, such as monostearin, pentaerythritol monoacetate and the like, and halogenated polyhydric alcohols such as the monochlorohydrins of glycerol, sorbitol, pentaerythritol and the like.

Another class of polymeric polyepoxides which can be amine cured and are in accordance with the present invention includes the epoxy novolac resins obtained by reacting, preferably in the presence of a basic catalyst, e.g., sodium or potassium hydroxide, an epihalohydrin, such as epichlorohydrin, with the resinous condensate of an aldehyde, e.g., formaldehyde, and either a monohydric phenol, e.g., phenol itself, or a polyhydric phenol. Further details concerning the nature and preparation of these epoxy novolac resins can be obtained in Lee, H. and Neville, K., Handbook of Epoxy Resins, McGraw Hill Book Co., New York, 1967.

The curing agent mixture is usually added to the epoxy base resin in such an amount that there is one reactive NH group in the curing component for each epoxy group in the epoxy resin component. These are known as stoichiometric quantities. The stoichiometric quantity can be calculated from the knowledge of the chemical structure and analytical data on the component.

For the purposes of the present invention, the stoichiometric amount of curing agent mixture is calculated by adding together the number of equivalents on the basis of wt % replaceable NH groups.

Stoichiometry unfortunately is not always calculable. The proper amount of curative to provide best properties is usually determined by the preparation of a number of samples which are tested to determine the composition with the most desirable physical characteristics. Typically, the physical property maximized is either the glass transition point (Tg) according to ASTM D-3418 or the heat deflection temperature (HDT) according to ASTM D-648.

This invention is shown by way of Example.

EXAMPLE

Cyclic carbonates were reacted with excess amine to yield carbamate reaction product mixtures which were used without additional purification to cure epoxy base resins. A series of samples was formulated for each curing agent epoxy resin mixture and the glass transition temperature (Tg) was determined by differential scanning calorimetry. The sample which yielded the maximum glass transition temperature was selected as the optimum ratio of curing agent/epoxy base resin reported in Table 1A. Tables 1A and 1B report the results.

It was found that the concentration of carbamate was determinative of epoxy resin properties. In general, the reactivity of the curing mixture was maximum (minimum gel time) at amine/carbonate molar ratios of 2/1 to 3/1. The cured resin modulus values, however, increase with decreasing amine/carbonate ratios.

Tables 2A and 2B report cured epoxy resins from higher molecular weight di-primary amines (which aminocarbamates from ethyleneamines as accelerators, e.g. TETA/PC) and their physical properties.

TABLE 1A

Epoxy Curing Properties and Glass Transition Temperatures with Ethyleneamine Carbamates and Their Solutions

| Example | reactants | mole ratio | gel time, min | visc., cps | $T_g$, °C. | max. exo., °C. |
|---|---|---|---|---|---|---|
| 1 | DETA/EC | 3 | 21 | 2600 | 113 | 258 |
| 2 | | 5 | 24 | 2000 | 125 | 261 |
| 3 | DETA/PC | 1 | 34 | 23000 | 76 | 192 |
| 4 | | 2 | 24 | 6000 | 102 | 243 |
| 5 | | 3 | 21 | 2700 | 104 | 250 |
| 6 | | 5 | 27 | 2150 | 118 | 259 |
| 7 | | 10 | 35 | 1900 | — | 262 |
| 8 | DETA | — | 40 | 1330 | 130 | 265 |
| 9 | TETA/EC | 1 | 35 | 25700 | 90 | 200 |
| 10 | | 2 | 21 | 6750 | 117 | 243 |
| 11 | | 3 | 23 | 3600 | 120 | 255 |
| 12 | | 5 | 17 | 1130 | 121 | 232 |
| 13 | TETA/PC | 1 | 28 | 28000 | 87 | 207 |
| 14 | | 2 | 24 | 7500 | 108 | 238 |
| 14 | | 3 | 24 | 3500 | 115 | 249 |
| 16 | | 5 | 24 | 2300 | 122 | 251 |
| 17 | | 10 | 34 | 2700 | 124 | 262 |
| 18 | TETA | — | 39 | 2500 | 130 | 250 |
| 19 | TEPA/EC | 1 | 23 | 18500 | 100 | 223 |
| 20 | | 2 | 24 | 7450 | 118 | 241 |
| 21 | TEPA/PC | 1 | 28 | 21500 | 102 | 190 |
| 22 | | 2 | 24 | 6800 | 112 | 241 |
| 23 | | 3 | 25 | 4800 | 123 | 249 |
| 24 | | 5 | 29 | 3520 | 124 | 255 |
| 25 | TEPA | — | 35 | 2100 | | 260 |
| 26 | EDR-148/PC | 2 | 38 | 1500 | 58 | 213 |
| 27 | | 3 | 36 | 900 | 67 | 226 |
| 28 | | 5 | 50 | 780 | 80 | 225 |
| 29 | EDR-148 | — | 85 | 610 | 96 | 240 |
| 30 | IPDA/PC | 2 | 55 | 45000 | 116 | 176 |
| 31 | | 6 | 105 | 5200 | 138 | 173 |
| 32 | IPDA | — | 180 | 2270 | 153 | 186 |
| 33 | MXDA/PC | 2 | 30 | 5500 | 88 | 223 |
| 34 | | 5 | 51 | 2000 | 100 | 223 |
| 35 | MXDA | — | 119 | 1050 | 119 | 231 |
| 36 | 1,3-DAP/PC | 2 | 53 | 2500 | 95 | 198 |
| 37 | 1,3-DAP | — | 65 | 350 | 114 | 222 |

Reactants refers to the amine/carbonate pair used in the reaction, and ratio is the molar ratio of amine to carbonate. Gel time is the time required for gelation of a 200 g mass of curing agent/epoxy resin (EPON ® 828) initially at 23° C. Visc. is the initial viscosity of the resin/curing agent solution, in centipoise. Max. exo. is the highest temperature reached during the cure as measured by an immersed thermocouple.

IPDA is isophoronediamine; MXDA is m-xylylenediamine; 1,3-DAP is 1,3-diaminopentane; EDR-148 is triethylene glycol diamine; EC and PC are ethylene and propylene carbonates.

EPON ® 828 is the glycidyl ether of bisphenol a, the condensation product of epichlorohydrin and bisphenol A, available from Shell Chemical Co.

TABLE 1B

Mechanical Properties of Epoxy Resins Cured with Ethyleneamine Carbamates and Their Solutions

| Example | reactants | mole ratio | flex. str., ksi | flex. mod., ksi | tens. str., ksi | tens. mod., ksi | elong., % |
|---|---|---|---|---|---|---|---|
| 1 | DETA/EC | 3 | 18.7 | 428 | 9.0 | 470 | 4 |
| 2 | | 5 | 15.8 | 414 | 7.6 | 442 | 2.5 |
| 3 | DETA/PC | 1 | 12.0 | 548 | 5.7 | 661 | 1.1 |
| 4 | | 2 | 18.7 | 464 | 8.3 | 512 | 2.1 |
| 5 | | 3 | 20.3 | 475 | 12 | 490 | 5.2 |
| 6 | | 5 | 17.7 | 428 | 9.6 | 461 | 4.1 |
| 7 | | 10 | 17.3 | 405 | 8.8 | 461 | 2.8 |
| 8 | DETA | — | 15.7 | 388 | 6.3 | 466 | 2.2 |
| 9 | TETA/EC | 1 | 21.5 | 504 | 10.3 | 585 | 2.7 |
| 10 | | 2 | 19.0 | 440 | 8.6 | 482 | 2.5 |
| 11 | | 3 | 17.2 | 422 | 9.4 | 418 | 3.6 |
| 12 | | 5 | 14.3 | 412 | 9.9 | 435 | 4.7 |
| 13 | TETA/PC | 1 | 16.9 | 530 | 7.0 | 632 | 1.3 |
| 14 | | 2 | 15.7 | 457 | 8.5 | 481 | 2.4 |
| 15 | | 3 | 17.3 | 437 | 10.1 | 468 | 4.0 |
| 16 | | 5 | 17.4 | 427 | 10.7 | 452 | 5.4 |
| 17 | | | | | | | |
| 18 | TETA | — | 13.1 | 392 | 7.6 | 434 | 4.0 |
| 19 | TEPA/EC | 1 | 20.3 | 470 | 9.0 | 501 | 2.4 |
| 20 | | 2 | 17.0 | 440 | 7.7 | 503 | 2.2 |
| 21 | TEPA/PC | 1 | 19.1 | 482 | 9.1 | 507 | 2.4 |
| 22 | | 2 | 18.7 | 444 | 6.8 | 482 | 1.8 |
| 23 | | 3 | 17.0 | 432 | 10.1 | 435 | 4.1 |
| 24 | | 5 | 17.3 | 412 | 9.7 | 438 | 3.7 |
| 25 | TEPA | — | 11.9 | 381 | 6.7 | 426 | 2.2 |
| 26 | EDR-148/PC | 2 | 17.6 | 467 | 8.98 | 537 | 2.4 |
| 27 | | 3 | 17.1 | 442 | 5.04 | 523 | 1.1 |
| 28 | | 5 | 15.9 | 418 | 8.05 | 470 | 5.0 |
| 29 | EDR-148 | — | 15.4 | 395 | 7.78 | 490 | 2.2 |
| 30 | IPDA/PC | 2 | | | | | |
| 31 | | 6 | | | | | |
| 32 | IPDA | — | | | | | |
| 33 | MXDA/PC | 2 | 16.9 | 567 | 5.24 | 617 | 0.92 |
| 34 | | 5 | 19.2 | 470 | 12.2 | 477 | 7.2 |
| 35 | MXDA | — | | | | | |
| 36 | 1,3-DAP/PC | 2 | 19.7 | 441 | 10.8 | 438 | 4.5 |
| 37 | 1,3-DAP | — | 15.7 | 420 | 11.8 | 452 | 5.0 |

Reactants and ratio are defined as in the previous table. Samples were cast in stainless steel molds (⅛" thick), and the room temperature flexural and tensile strength and modulus in thousands of psi (ksi) were determined.

TABLE 2A

Epoxy Curing Properties of JEFFAMINE ® D-230/Aminocarbamate Solutions

| Example | ratio | gel time, min | visc., cps | max. exo., °C. |
|---|---|---|---|---|
| 38 | 2.32 | 37 | 7430 | 212 |
| 39 | 1.39 | 44 | 4400 | 213 |
| 40 | 1.00 | 59 | 3300 | 190 |
| 41 | 0.53 | 150 | 1700 | 165 |
| 42 | 0 | — | 1250 | 64 |

The TETA/PC aminocarbamate accelerator (prepared with 1/1 ratio) was mixed with JEFFAMINE D-230; ratio refers to the ratio of amine equivalents from aminocarbamate/amine equivalents from the D-230 amine. All other headings have the same meaning as in Table 1.

JEFFAMINE ® D-230 structural formula:

$H_2NCH(CH_3)CH_2$—$[OCH_2CH(CH_3)]_x$—$NH_2$ wherein x averages 2.6.

TABLE 2B

Mechanical Properties of Epoxy Resins Cured with JEFFAMINE ® D-230/Aminocarbamate Solutions

| Example | ratio | flex. str., ksi | flex. mod., ksi | tens. str., ksi | tens mod., ksi | elong., % |
|---|---|---|---|---|---|---|
| 38 | 2.32 | 19.6 | 491 | 11.5 | 459 | 5.93 |
| 39 | 1.39 | 19.3 | 476 | 9.75 | 481 | 3.34 |
| 40 | 1.00 | 18.7 | 468 | 10.7 | 460 | 8.99 |
| 41 | 0.53 | 17.5 | 453 | 7.89 | 443 | 2.29 |
| 42 | 0 | 15.7 | 454 | 9.8 | 417 | 4.70 |

Ratio has the same meaning as in the previous table; all other headings have the same meaning as in Table 2.

TABLE OF TEST METHODS

| | |
|---|---|
| Gel Time (minutes) | ASTM D-2471-71 |
| Elongation at Break (%) | ASTM D-638 |
| Tensile Strength (psi) | ASTM D-638 |
| Tensile Modulus (psi) | ASTM D-638 |
| Flexural Strength (psi) | ASTM D-790 |
| Flexural Modulus (psi) | ASTM D-790 |
| Heat Deflection Temperature (HDT) (°C., 264 psi/66 psi) | ASTM D-648 |
| Glass Transition Point (Tg) (°C.) | ASTM D-3418 |

While particular embodiments of the invention have been described, it will be understood, of course, that the invention is not limited thereto since many modifications may be made, and it is, therefore, contemplated to cover by the appended claims any such modification as fall within the true spirit and scope of the invention.

What is claimed is:

1. An epoxy resin composition comprising the cured reaction product of an epoxy resin and a curing agent, the curing agent comprising: a mixture of an ethylene carbamate selected from the group consisting of:

$H_2NCH_2CH_2(NHCH_2CH_2)_xNH$—$COOCH_2CH(R_1)OH$; and $H_2NCH_2CH_2(NHCH_2CH_2)_xNH$—$COOCH_2(R_2)OH$ and mixtures thereof, and an ethylene amine of the formula:

$H_2NCH_2CH_2(NHCH_2CH_2)_xNH_2$ wherein:
x ranges from 0 to 5, and
$R_1$ is a radical selected from the group consisting of hydrogen, methyl and ethyl, and
wherein in the mixture the molar ratio of ethylene amine:ethylene aminocarbamate ranges from 1:1 to 2:1.

2. The epoxy resin composition of claim 1 wherein x ranges from 1 to 3.

3. The epoxy resin composition of claim 1 wherein $R_1$ is a methyl or ethyl radical.

4. The epoxy resin composition of claim 1 wherein x ranges from 1 to 3 and $R_1$ is a methyl or ethyl radical.

5. An epoxy resin composition comprising the cured reaction product of an epoxy resin and a curing agent, the curing agent comprising: a mixture of an ethylene glycol aminocarbamate selected from the group consisting of:

$H_2NCH_2CH_2(OCH_2CH_2)_xNH$—$COOCH_2CH(R_1)OH$;

$H_2NCH_2CH_2(OCH_2CH_2)_xNH$—$COOCH_2(R_1)CH_2OH$ and mixtures thereof, and an ethylene glycol diamine of the formula:

$H_2NCH_2CH_2(OCH_2CH_2)_xNH_2$ wherein:
x ranges from 0 to 5, and
$R_1$ is a radical selected from the group consisting of hydrogen methyl and ethyl, and
wherein in the mixture the molar ratio of ethylene glycol diamine:ethylene carbamate ranges from 1:1 to 2:1.

6. The epoxy resin composition of claim 5 wherein x ranges from 1 to 4.

7. The epoxy resin composition of claim 5 wherein $R_1$ is a methyl or ethyl radical.

8. The epoxy resin composition of claim 5 wherein x ranges from 1 to 4 and $R_1$ is a methyl or ethyl radical.

9. An epoxy resin composition comprising the cured reaction product of an epoxy resin and a curing agent, the curing agent comprising: a mixture of a cycloaliphatic carbamate selected from the group consisting of:

$H_2NCH_2$—Ph—$CH_2NH$—$COOCH_2CH(R_1)OH$; and $H_2NCH_2$—Ph—$CH_2NH$—$COOCH(R_1)CH_2OH$
and mixtures thereof and a cycloaliphatic diamine of the formula:

$H_2NCH_2$—Ph—$CH_2NH_2$ wherein:
Ph is a 1,3-phenylene or 1,4-phenylene radical and $R_1$ is a radical selected from the group consisting of hydrogen, methyl and ethyl, and wherein in the mixture the molar ratio of cycloaliphatic diamine:cycloaliphatic carbamate ranges from 0:1 to 10:1.

10. The composition of claim 9 wherein Ph is a 1,3-phenylene radical.

11. An epoxy resin composition comprising the cured reaction product of an epoxy resin and a curing agent, the curing agent comprising: a mixture of an alkyl carbamate selected from the group consisting of:

$H_2N-R-NH-COOCH_2(R_1)OH$; and $H_2N-R-NH-COOCH(R_1)CH_2OH$ and mixtures thereof, and an alkylene deamine of the formula:

$H_2N-R-NH_2$ wherein:
R is an alkylene radical of 2 to 20 carbon atoms, and
$R_1$ is a radical selected from the group consisting of hydrogen, methyl and ethyl, and
wherein in the mixture the molar ratio of alkylene diamine:alkyl carbamate ranges from 0.1:1 to 10:1.

12. The composition of claim 11 wherein R is a 1,3-pentylene radical.

13. An epoxy resin composition comprising the cured reaction product of an epoxy resin and a curing agent, the curing agent comprising: a mixture of a cycloaliphatic carbamate selected from the group consisting of:

$H_2N-IPh-NH-COOCH_2CH(R_1)OH$, and $H_2N-IPh-NH-COOCH(R_1)CH_2OH$ and mixtures thereof, and a cycloaliphatic diamine of the formula:

$H_2N-IPh-NH_2$ wherein:
$R_1$ is a radical selected from the group consisting of hydrogen, methyl and ethyl, and
IPh is an isophorone radical of the formula:

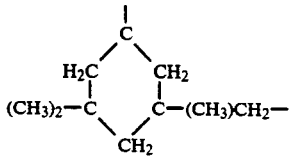

and wherein in the mixture the molar ratio of cycloaliphatic diamine:cycloaliphatic carbamate ranges from 0.1:1 to 10:1.

* * * * *

UNITED STATES PATENT AND TRADEMARK OFFICE
CERTIFICATE OF CORRECTION

PATENT NO. : 5,235,007
DATED : August 10, 1993
INVENTOR(S) : David Christopher Alexander, Wheeler Conrad Crawford, and Howard Paul Klein It is certified that error appears in the above-indentified patent and that said Letters Patent is hereby corrected as shown below:

Column 8, claim 1, lines 1-5 should read as follows:

$H_2NCH_2CH_2(NHCH_2CH_2)_xNH-COOCH_2CH(R_1)OH;$ and $H_2NCH_2CH_2(NHCH_2CH_2)_xNH-COOCH_2(R_1)CH_2OH$ and mixtures thereof, Signed and Sealed this Seventh Day of February, 1995

Attest:

BRUCE LEHMAN

*Attesting Officer*   *Commissioner of Patents and Trademarks*